United States Patent
Tegels (10) Patent No.: US 10,010,312 B2
(45) Date of Patent: Jul. 3, 2018

(54) DISTAL RAPID EXCHANGE FOR TRANSLUMINAL ANGIOPLASTY DEVICE AND METHODS

(71) Applicant: ST. JUDE MEDICAL PUERTO RICO LLC, Caguas, PR (US)

(72) Inventor: Zachary J. Tegels, Minneapolis, MN (US)

(73) Assignee: St. Jude Medical Puerto Rico LLC, Caguas, PR (US)

(*) Notice: Subject to any disclaimer, the term of this patent is extended or adjusted under 35 U.S.C. 154(b) by 879 days.

(21) Appl. No.: 13/787,470

(22) Filed: Mar. 6, 2013

(65) Prior Publication Data

US 2014/0257371 A1 Sep. 11, 2014

(51) Int. Cl.
A61B 17/00 (2006.01)

(52) U.S. Cl.
CPC .. *A61B 17/0057* (2013.01); *A61B 2017/0065* (2013.01); *A61B 2017/00526* (2013.01); *A61B 2017/00654* (2013.01); *A61B 2017/00672* (2013.01)

(58) Field of Classification Search
CPC ...... A61B 17/0057; A61B 2017/00672; A61B 2017/00654; A61B 2017/00526; A61B 2017/0065
USPC ................................. 606/213–215
See application file for complete search history.

(56) References Cited

U.S. PATENT DOCUMENTS

| | | | |
|---|---|---|---|
| 5,383,853 A * | 1/1995 | Jung | A61M 25/0068 604/103.04 |
| 5,458,639 A * | 10/1995 | Tsukashima | A61M 25/104 604/102.02 |
| 5,690,642 A * | 11/1997 | Osborne | A61F 2/958 604/103.04 |
| 5,713,854 A * | 2/1998 | Inderbitzen | A61M 25/104 604/509 |
| 5,728,132 A | 3/1998 | Van Tassel et al. | |
| 6,123,718 A * | 9/2000 | Tu | A61B 18/1492 606/41 |
| 6,190,393 B1 | 2/2001 | Bevier et al. | |
| 6,475,182 B1 * | 11/2002 | Hnojewyj | B01F 13/0023 604/191 |
| 7,815,600 B2 | 10/2010 | Al-Marashi et al. | |
| 2002/0144696 A1 * | 10/2002 | Sharkawy | A61B 17/11 128/898 |
| 2004/0093044 A1 * | 5/2004 | Rychnovsky | A61B 18/245 607/88 |

(Continued)

OTHER PUBLICATIONS

PCT International Search Report for International Application No. PCT/US14/19890, dated Aug. 8, 2014 (4 pp.).

*Primary Examiner* — Tuan V Nguyen
*Assistant Examiner* — Socrates L Boutsikaris
(74) *Attorney, Agent, or Firm* — Dorsey & Whitney LLP (57) ABSTRACT

A vascular closure device includes a catheter, a balloon, an introducer, and a guidewire lumen. The catheter includes an inflation lumen. The balloon is positioned at a distal end portion of the catheter. The introducer is positioned distal of the balloon. The guidewire lumen extends along at least a portion of the introducer and terminates at a rapid exchange port positioned distal of the balloon. The guidewire lumen is receptive of a guidewire to guide the catheter through a vessel puncture in a vessel to position the balloon within the vessel.

11 Claims, 12 Drawing Sheets

(56) References Cited

U.S. PATENT DOCUMENTS

| | | | |
|---|---|---|---|
| 2006/0229670 A1* | 10/2006 | Bates | A61B 17/0057 |
| | | | 606/213 |
| 2008/0046005 A1* | 2/2008 | Lenker | A61B 17/00491 |
| | | | 606/214 |
| 2012/0143139 A1 | 6/2012 | Min et al. | |
| 2013/0046376 A1 | 2/2013 | Hassan et al. | |
| 2014/0018732 A1* | 1/2014 | Bagaoisan | A61M 25/0147 |
| | | | 604/95.04 |

* cited by examiner

FIG. 5B ial Field

DISTAL RAPID EXCHANGE FOR TRANSLUMINAL ANGIOPLASTY DEVICE AND METHODS

TECHNICAL FIELD

The present disclosure relates to closure devices, and more specifically relates to closure devices that temporarily seal a vessel puncture.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., a catheter) may pass through the sheath and to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral vascular punctures, may be stopped by utilizing vascular closure devices.

Typical closure devices position an anchor member through the puncture for at least partial sealing of the puncture internally. An insertion sheath is usually pre-positioned extending through the puncture to provide an unobstructed path for inserting the closure device through puncture to position the anchor within the vessel. In at least some closure procedures, a sheath exchange is required to exchange a procedural sheath, which is compatible with treatment devices to treat the vessel, with an insertion sheath compatible with the closure device. Using insertion sheaths as part of a puncture closure procedure may have a number of drawbacks, including the need for a sheath exchange, which may be time-consuming and add complexity to the closure procedure. Opportunities exist for improvements in puncture closure devices and related methods of closing a puncture.

SUMMARY

One aspect of the present disclosure relates to a vascular closure device having a catheter, a balloon, an introducer, and a guidewire lumen. The catheter includes an inflation lumen. The balloon is positioned at a distal end portion of the catheter. The introducer is positioned distal of the balloon. The guidewire lumen extends along at least a portion of the introducer and terminates at a rapid exchange port positioned distal of the balloon. The guidewire lumen is receptive of a guidewire to guide the catheter through a vessel puncture in a vessel to position the balloon within the vessel.

The rapid exchange port may be positioned at a distal bond location between the catheter and the introducer. The rapid exchange port may be positioned at a distal bond location between the introducer and a distal waist of the balloon. The vascular closure device may further include a stiffening wire extending along at least a portion of the catheter to the rapid exchange port. The stiffening wire may be positioned in the inflation lumen.

The guidewire lumen may extend from a distal tip of the introducer proximally to the rapid exchange port. The introducer, catheter and a distal waist of the balloon may be heat bonded together. The balloon, when inflated, may be configured to abut against an internal wall of the vessel to temporarily seal the vessel puncture. The catheter may include a blood flashback lumen having a distal opening at a location proximal of the balloon.

Another aspect of the present disclosure relates to a vascular closure device having an inflation tube, a balloon, and a guidewire lumen. The inflation tube includes an inflation lumen. The balloon is mounted to the inflation tube and arranged in flow communication with the inflation lumen. The balloon is inflatable to temporarily seal a vessel puncture intravascularly. The guidewire lumen extends distally from the balloon from a proximal port to a distal port. The guidewire lumen is receptive of a guidewire. The vascular closure device is configured for advancement along the guidewire and through the vessel puncture.

The vascular closure device further includes an introducer positioned distal of the balloon and defining the guidewire lumen. The inflation tube may include a blood flashback lumen having a distal opening arranged proximal of the balloon. The vascular closure device may further include a stiffening wire extending proximally from the proximal port of the guidewire lumen. The vascular closure device may further include a distal balloon bond arranged between a distal waist of the balloon and the inflation tube, and the proximal port of the guidewire lumen may be positioned at the distal balloon bond. The vascular closure device may further include a sealing member positioned outside of the vessel puncture and configured to seal the vessel puncture extravascularly.

A further aspect of the present disclosure relates to a method of sealing a vessel puncture in a vessel. The method includes providing a guidewire and a vascular closure device, the vascular closure device having a catheter, a balloon, and an introducer, the introducer having a guidewire lumen with proximal and distal ports, and the proximal port being positioned distal of the balloon. The method further includes inserting a distal end of the guidewire through a vessel puncture, inserting a proximal end of the guidewire into the distal port of the introducer and out through the proximal port of the introducer, advancing the vascular closure device along the guidewire to position the introducer and balloon through the vessel puncture, inflating the balloon, and abutting the inflated balloon against an inner surface of the vessel to temporarily seal the vessel puncture.

The method may include delivering sealing material to an external surface of the vessel to seal the vessel puncture externally. The method may include deflating the balloon and removing the vascular closure device through the delivered sealing material. The method may include providing an insertion sheath and inserting the insertion sheath through the vessel puncture before inserting the guidewire, and after removing the guidewire, removing the insertion sheath before advancing the vascular closure device along the guidewire.

Another aspect of the present disclosure relates to a method of closing a vessel puncture in a vessel. The method includes providing an insertion sheath, a guidewire, and a vascular closure device having a balloon and a guidewire lumen, the guidewire lumen having a rapid exchange port positioned distal of the balloon. The method further includes inserting the insertion sheath through the vessel puncture, inserting the guidewire through the vessel puncture, withdrawing the insertion sheath while maintaining the guidewire in the vessel puncture, inserting a proximal end of the guidewire into the guidewire lumen and out through the rapid exchange port, advancing the vascular closure device along the guidewire to position the balloon through the vessel puncture, and inflating the balloon to temporarily close the vessel puncture internally.

The method may include withdrawing the vascular closure device in a proximal direction to abut the inflated balloon against an inner surface of the vessel adjacent to the vessel puncture. The method may include depositing a sealing material adjacent to the vessel puncture along an exterior surface of the vessel to seal the vessel puncture, and removing the balloon through the deposited sealing material.

Another example method in accordance with the present disclosure relates to a method of forming a vascular closure device. The method includes providing an inflation tube having a distal end portion, a balloon having a distal waist, and an introducer having a guidewire lumen with a proximal port, inserting a mandrel through the guidewire lumen and out of the proximal port, the mandrel overlapping the distal waist and the distal end portion of the inflation tube, and applying heat to bond the guidewire lumen, inflation tube and distal waist together.

The method may include removing the mandrel to expose the proximal port at a location distal of the balloon. The method may include skiving a proximal end of the guidewire lumen before inserting the mandrel. The method may include flattening a distal end portion of the inflation tube before applying heat. The method may include cutting a tab in the distal end portion of the inflation tube before applying heat.

The foregoing and other features, utilities, and advantages of the invention will be apparent from the following detailed description of the invention with reference to the accompanying drawings.

DETAILED DESCRIPTION

As mentioned above, vascular procedures are conducted throughout the world and require access to a vessel through a puncture. Most often, the vessel is a femoral artery. To close the puncture following completion of the procedure, many times a closure device is used to sandwich the puncture between an anchor and a sealing plug. In other closure procedures, a temporary sealing member such as an inflatable balloon is positioned external the vessel and expanded to seal the puncture internally while a sealing material is delivered to an internal surface of the vessel to seal the puncture externally. The temporary sealing member is then refracted through the delivered sealing material.

While the vascular instruments shown and described below include procedural sheaths and puncture closure devices, the application of principles described herein are not limited to the specific devices shown. The principles described herein may be used with any medical device. Therefore, while the description below is directed primarily to arterial procedures and certain embodiments of a vascular closure device, the methods and apparatus are only limited by the appended claims. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

As used in this specification and the appended claims, the term "engage" and "engagable" are also used broadly to mean interlock, mesh, or contact between two devices. A "tube" is an elongated device with a passageway. The passageway may be enclosed or open (e.g., a trough). A "lumen" refers to any open space or cavity in a bodily organ, especially in a blood vessel. The words "including" and "having," as used in the specification, including the claims, have the same meaning as the word "comprising."

The present disclosure describes a medical device such as a tissue puncture closure device that is capable of closing a tissue puncture such as a vessel puncture. The tissue puncture closure device may include a guidewire rapid exchange port. The rapid exchange port may be positioned distal of an anchor member of the tissue puncture closure device. In at least some examples, the anchor is an inflatable balloon. The anchor may be referred to as a temporary sealing member or a feature that provides temporary hemostasis during delivery of a sealing material to an external surface of the tissue layer (e.g., vessel wall). The tissue puncture closure device may include a guidewire lumen positioned distal of the anchor. A proximal port of the guidewire lumen may provide a rapid exchange port for the guidewire to exit the tissue puncture closure device at a location distal of the anchor.

Generally, the function of the tissue puncture closure device is to provide a guidewire lumen distal of an anchor (e.g., balloon) for temporarily sealing the tissue puncture internally as part of an extravascular closure procedure. An extravascular closure procedure includes delivery of a sealing material to an external surface of the tissue layer (e.g., vessel wall) to seal the puncture. The anchor (e.g., balloon) is withdrawn through the sealing material. Typically, no features remain positioned within the vessel after completion of the closure procedure. The guidewire lumen, which is arranged distal of the anchor, may provide the ability to perform an extravascular closure procedure without using a sheath.

An additional function of the tissue puncture closure device as disclosed herein may be the ability to allow for a lower profile balloon angioplasty catheter. Positioning a rapid exchange guidewire port and guidewire lumen at a location distal of the balloon may eliminate the need for an additional lumen that receives the guidewire proximal of the balloon. Typically, a dual lumen or coaxial lumen catheter shaft is required if the guidewire extends within the catheter at a location proximal of the balloon. Removing the guidewire lumen from the catheter shaft at a location proximal of the balloon may permit significant reduction in the outer profile for the device, which may be particularly useful when crossing relatively tight lesions or chronic total occlusions (CTOs) in a vessel.

The tissue puncture closure device may include a distal bond between the distal waist of a balloon anchor member, an introducer tubing member extending distal of the balloon, and a distal balloon inflation leg or tubing to which the balloon is mounted. A distal portion of a core wire may be included in the distal bond to provide additional support near the bond. The core wire may limit kinking near the bond.

Extravascular tissue puncture closure devices typically rely on operation through an insertion sheath, which imposes device size limitations, extra operational steps, and unnecessary complexity in a closure procedure. Providing the tissue puncture closure device with an introducer feature and a guidewire rapid exchange port distal of the anchor may allow a low profile device construction that is operable without the use of a sheath. In at least some examples, the sheath may be withdrawn from the tissue puncture and remain mounted to the guidewire during operation of the tissue puncture closure device to seal the vessel puncture.

The present disclosure may also provide a reduced profile balloon catheter as described above, by moving the rapid exchange port and associated distal bond to a location distal of the anchor (e.g., balloon). This construction may eliminate the need for a coaxial device construction proximal of the balloon, and may provide an overall lower device profile for traversing lesions like CTOs. The distal bond may provide a bond between the introducer, balloon, and catheter shaft in a single step, while concurrently forming the proximal rapid exchange port for the guidewire lumen. The distal bond construction may eliminate additional assembly steps that may otherwise be needed to bond the parts together and form the rapid exchange guidewire port during manufacture.

Figure 1:
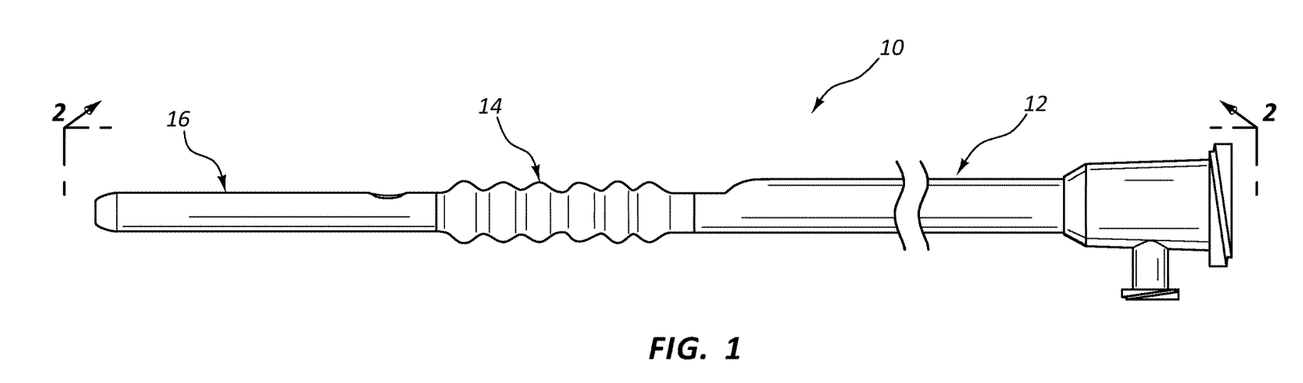
FIG. 1 is a side view of an example vascular closure device in accordance with the present disclosure.
Figure 2:
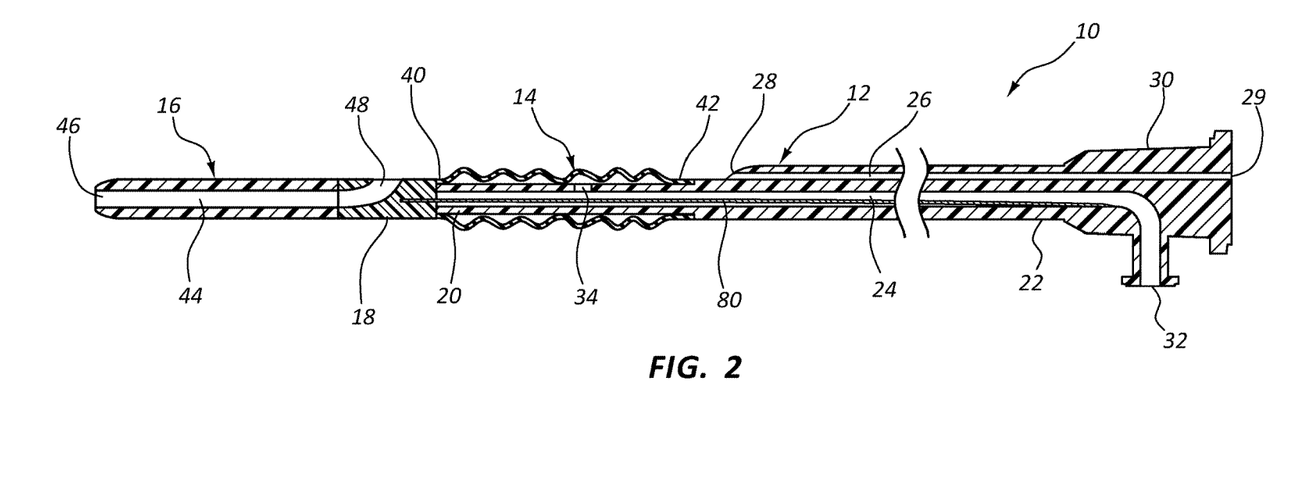
FIG. 2 is a cross-sectional view of the vascular closure device of FIG. 1 taken along cross-section indicators 2-2.

Referring now to FIGS. 1 and 2, an example vascular closure device 10 is shown including a catheter shaft 12, a balloon 14, an introducer 16, and a distal bond 18. As shown in FIG. 2, the catheter shaft 12 includes distal and proximal end portions 20, 22, an inflation lumen 24, an optional blood flashback lumen 26, a hub 30, an inflation inlet port 32, and an inflation outlet 34. The blood flashback lumen 26 may include a distal port 28 and a proximal port 29. The balloon 14 may include distal and proximal waists 40, 42. The distal bond 18 may be positioned distal of the balloon 14.

The introducer 16 may include a guidewire lumen 44 having distal and proximal ports 46, 48. The guidewire lumen 44 may extend along an entire length of the introducer 16. The proximal port 48 may be positioned distal of the balloon 14. The guidewire lumen 44 may be sized to receive a guidewire, wherein a proximal end of the guidewire is fed through the distal port 46 and out through the proximal port 48. A distal end of the guidewire is pre-positioned extending through a vessel puncture. The vascular closure device 10 is advanced along the guidewire to position the introducer 16 and balloon 14 extending through the vessel puncture as will be described in further detail below.

A core wire 80 may extend through the inflation lumen 24 of the catheter shaft 12. The core wire 80 may extend to the distal bond 18. The core wire 80 may provide stiffening of the vascular closure device 10 particularly in the area of the distal bond 18 and proximal port 48. The core wire 80 may help reduce the chance of kinking or undesirable bending of the vascular closure device 10 in the area of the distal bond 18.

The inflation inlet port 32 may be coupled to a source of inflation fluid. The inflation fluid may be delivered through the inflation lumen 24 and out through the inflation outlet 34 and into an interior of balloon 14 to inflate the balloon 14. The vascular closure device 10 may be withdrawn in a proximal direction to abut the inflated balloon 14 against the inner surface of the vascular adjacent to the vessel puncture to at least temporarily occlude blood flow through the vessel puncture (e.g., temporary hemostasis). The inflated balloon, when abutting against an internal surface of the vessel, may also provide a backstop that prevents a sealing material, which is used to seal the vessel puncture externally, from advancing through the vessel puncture into an interior of the vessel. After the sealing material is at least partially cured, the balloon 14 may be deflated and the vascular closure device 10 is withdrawn through the sealing material.

Figure 3A:
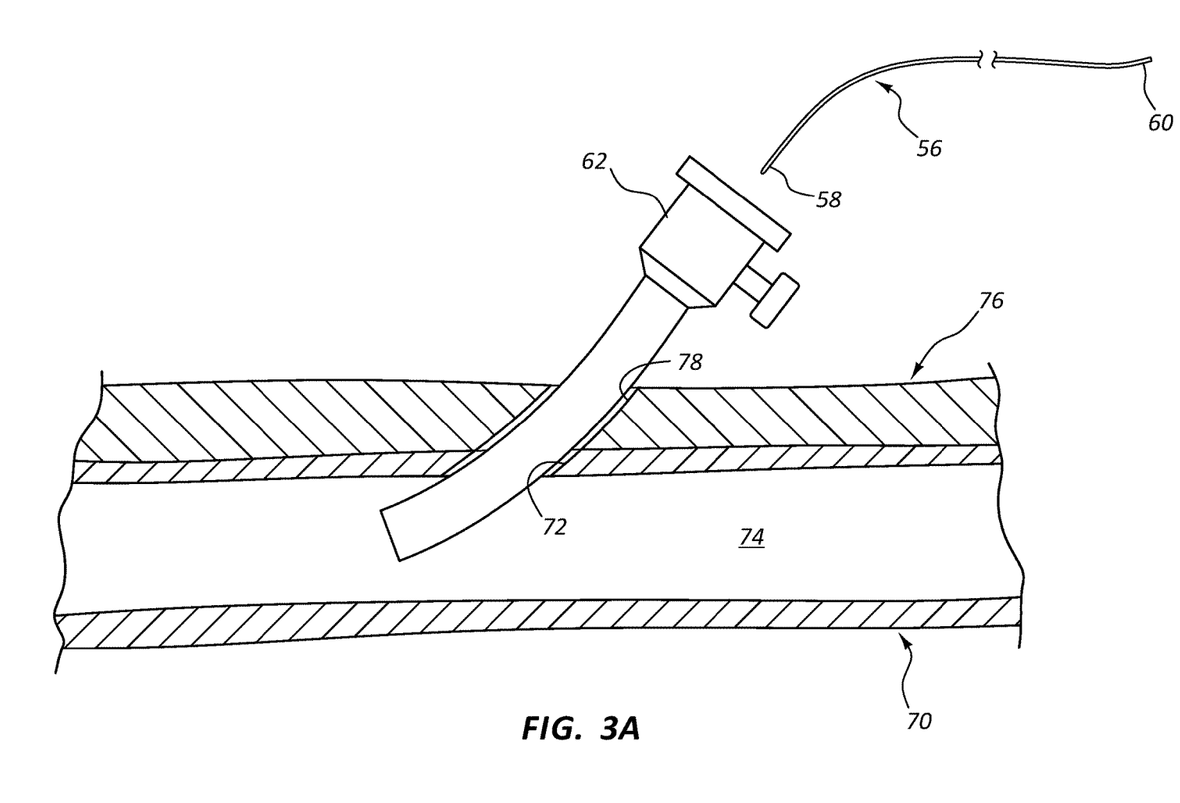
FIGS. 3A-3H show method steps for sealing a vessel puncture using the vascular closure device of FIG. 1.

Referring now to FIGS. 3A-3H, an example method of sealing a vessel puncture using the vascular closure device 10 is described in detail. FIG. 3A shows an insertion sheath 62 advanced through a vessel puncture 72 of a vessel 70 and into a vessel lumen 74. The insertion sheath 62 may pass through a tissue puncture 78 of a tissue layer 76 to reach the vessel puncture 72. The tissue puncture 78 may be referred to as percutaneous puncture. The tissue puncture 78 may also be referred to as a tissue tract.

Figure 3B:
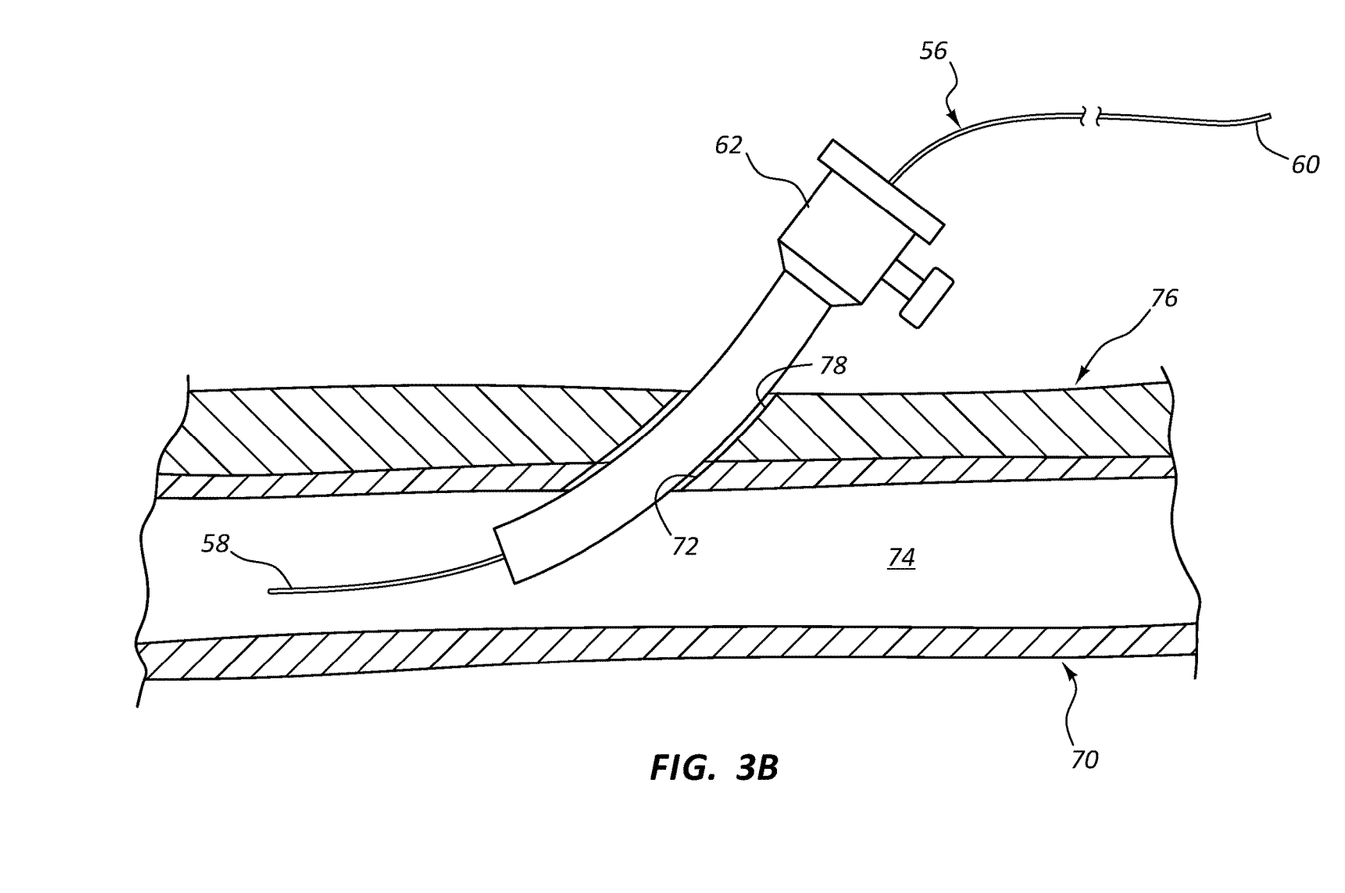

A guidewire 56 having distal and proximal ends 58, 60 may be advanced through an internal lumen of the insertion sheath 62 to position the guidewire 56 extending into the vessel lumen 74, as shown in FIG. 3B. The insertion sheath 62 may be positioned extending through the vessel puncture 72 and used as part of a treatment method in which at least one treatment device is delivered through the insertion sheath 62 to treat a patient intravascularly.

Figure 3C:
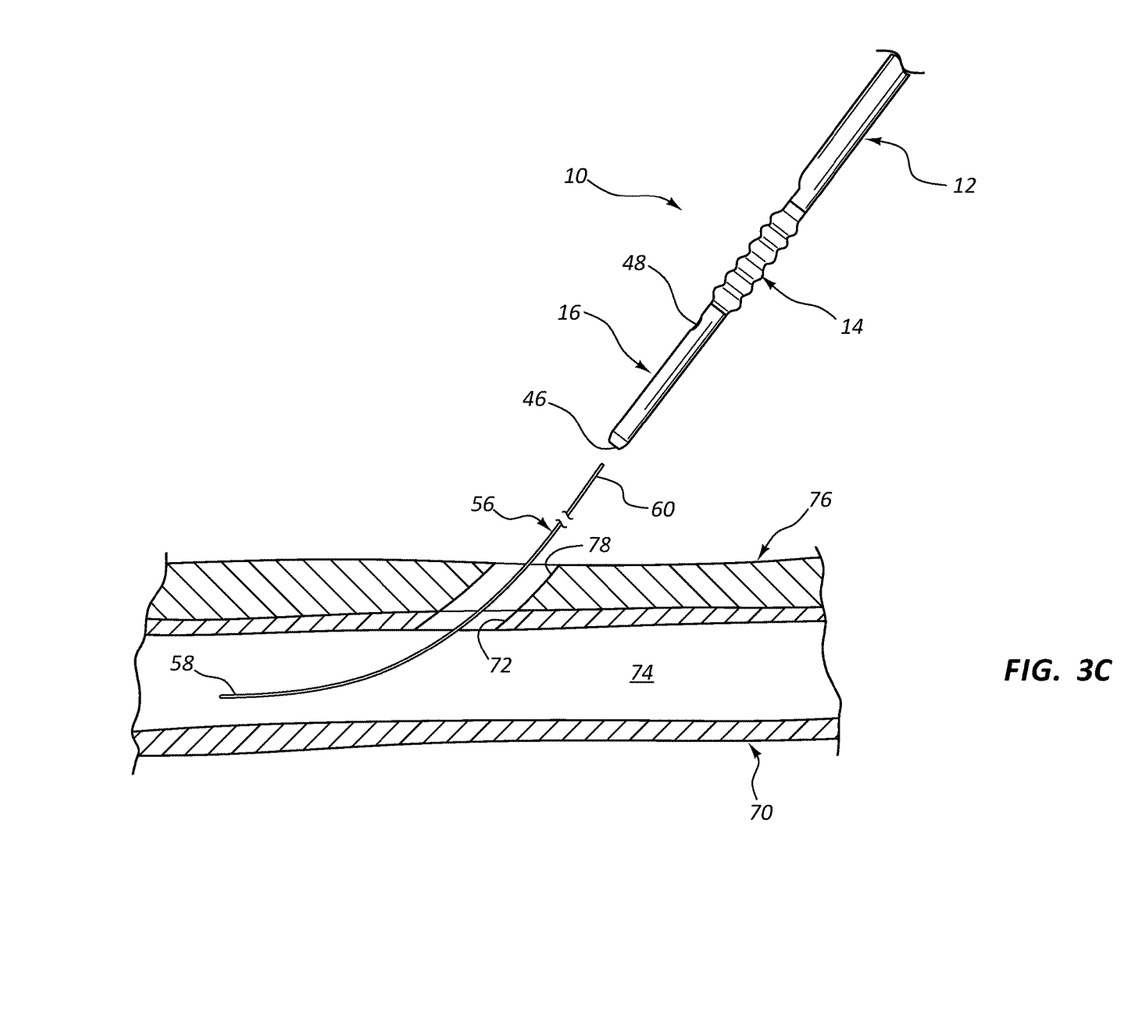

The insertion sheath 62 may be removed from the vessel puncture 72 while leaving behind the guidewire 56 as shown in FIG. 3C. The guidewire 56 may then be used to guide the vascular closure device 10 through the vessel puncture 72 and into the vessel lumen 74. The vascular closure device 10 may be used to seal the vessel puncture 72 without the use of insertion sheath 62 or any other sheath that provides access into the vessel lumen 74. Removing the insertion sheath 62 prior to advancing the vascular closure device to the vessel puncture may remove at least some restrictions on the size of an outer profile of the vascular closure device 10, particularly at the proximal end portion 22 of the catheter shaft. The size and shape of hub 30 may also be unrestricted since the vascular closure device 10 does not have to pass through the insertion sheath 62. In some arrangements, the insertion sheath 62 may be withdrawn from the vessel puncture 72 and the tissue puncture 78 while remaining positioned on the guidewire 56. The vascular closure device 10 may be advanced along the guidewire 56 through the insertion sheath 62. The length of the vascular closure device 10 may be sufficient to permit the hub 30 to remain outside of the insertion sheath 62 while operating the vascular closure device 10 to seal the vessel puncture 72.

Figure 3D:
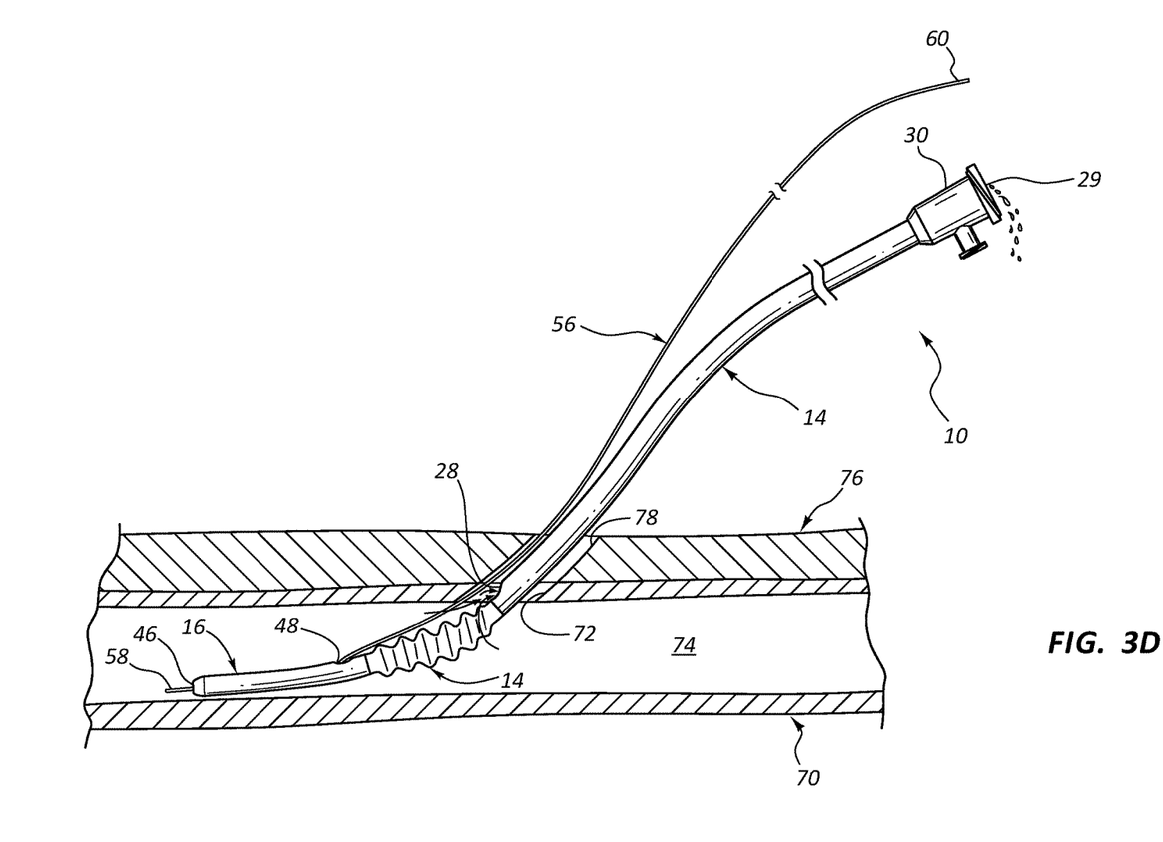

Referring again to FIG. 3C, the proximal end 60 of guidewire 56 may be aligned with the distal port 46 of the introducer 16. The guidewire 56 may be inserted into the distal port 46 and extend out through the proximal port 48. The vascular closure device may advance along the guidewire 56 and into the vessel lumen 74 as shown in FIG. 3D. The guidewire 56 may extend adjacent to the vascular closure device 10 proximal of the proximal port 48. Blood may flow into distal port 28 of the blood flashback lumen 26 and out through the proximal port 29 to provide a visual indicator to the operator that the distal port 28 is positioned within the vessel lumen 74 and exposed to blood flow therein.

Figure 3E:
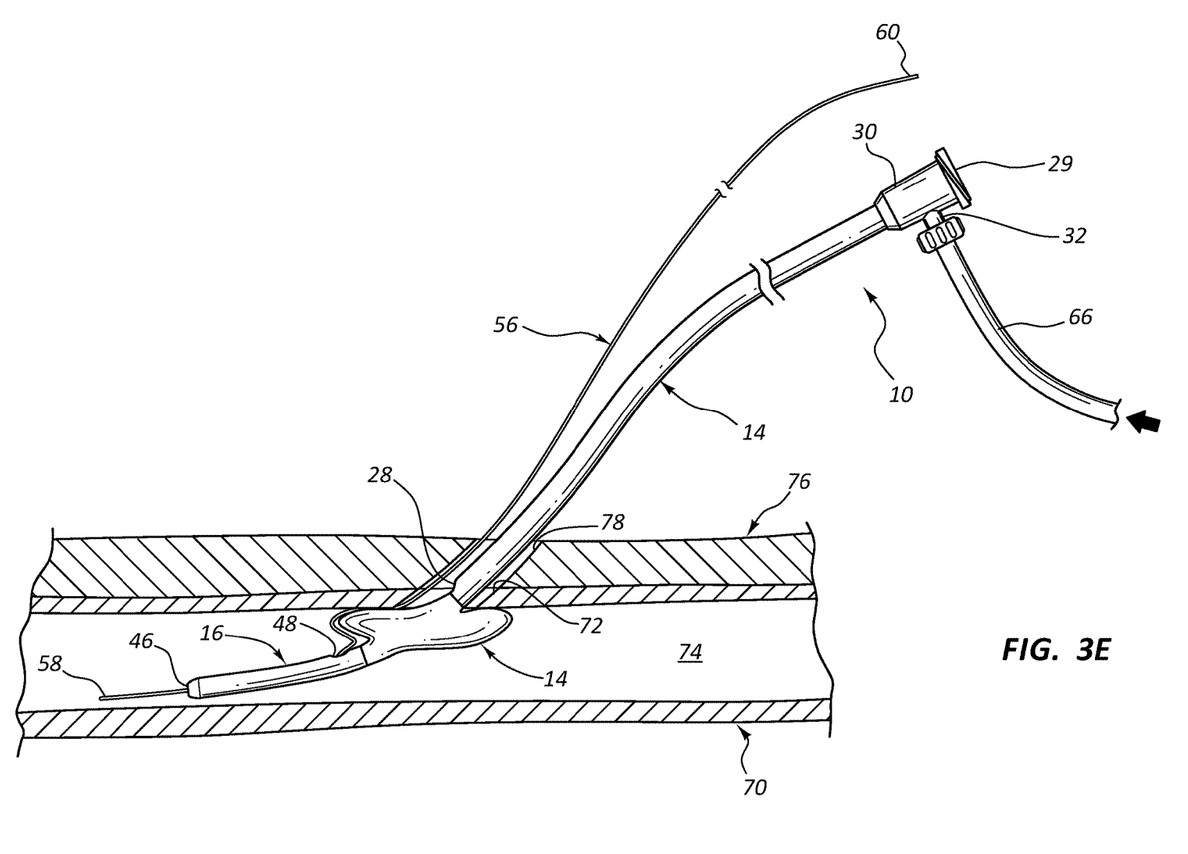

Referring to FIG. 3E, an inflation source 66 is connected to the inflation inlet port 32 to provide a volume of inflation fluid to balloon 14. After the balloon 14 is inflated, the vascular closure device 10 is withdrawn in a proximal direction to abut the inflated balloon 14 against the inner surface of the vessel 70 adjacent to vessel puncture 72. The inflated balloon 14 provides at least temporary hemostasis through vessel puncture 72. Blood flow through distal port 28 of the blood flashback lumen 26 may cease, thereby providing a visual indicator to the operator that the balloon 14 has temporarily sealed the vessel puncture 72.

Figure 3F:
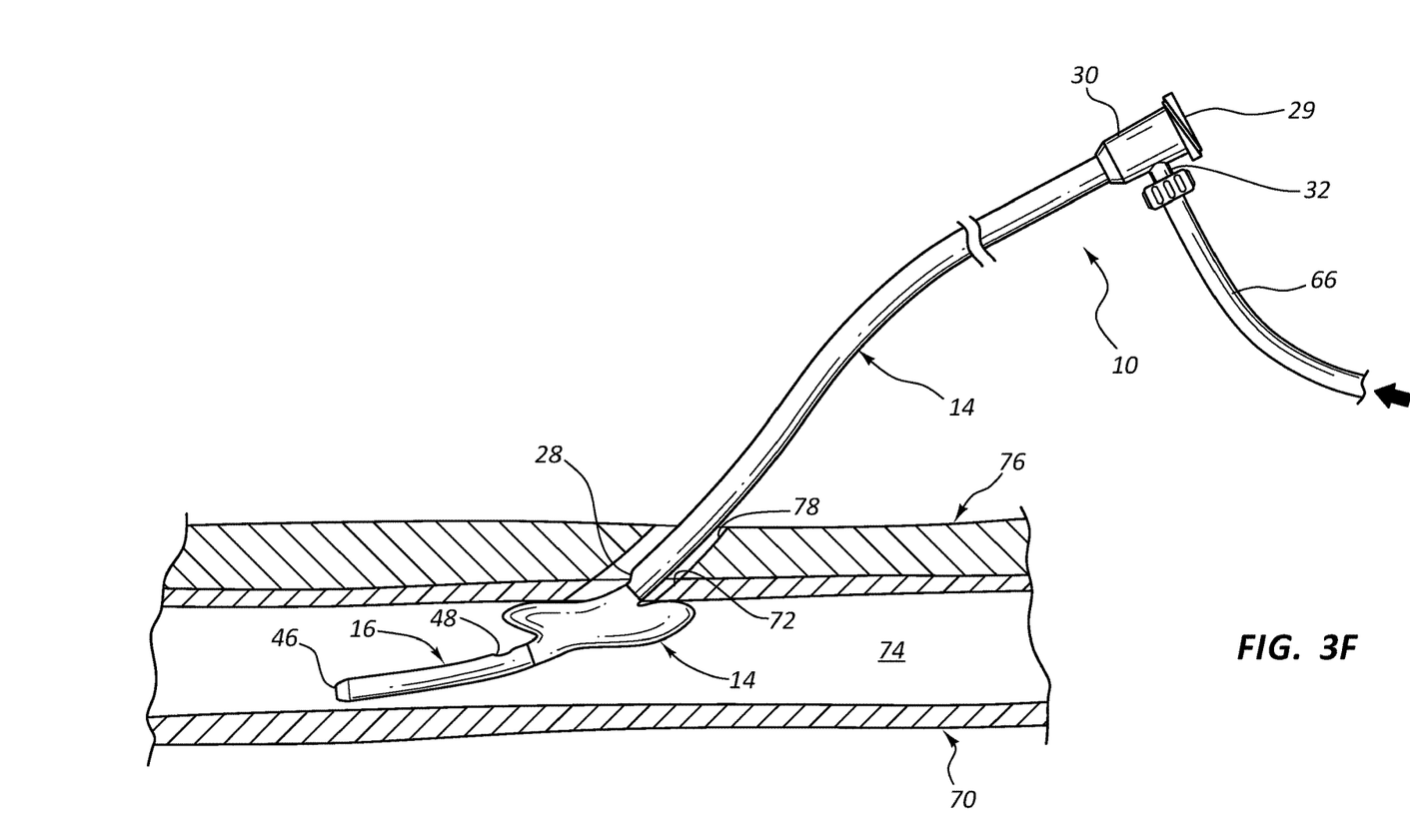

The guidewire 56 may remain positioned extending through the guidewire lumen 44 while the balloon 14 is inflated and providing temporary hemostasis of the vessel puncture 72 as shown in FIG. 3E. Alternatively, the guidewire 56 may be removed prior to providing temporary hemostasis with the inflated balloon 14 as shown in FIG. 3F. Typically, the guidewire 56 remains positioned extending through the vessel puncture 72 to insure access through the vessel puncture in the event the operator needs to re-enter the vessel 70 (e.g., if hemostasis is not maintained after removing the vascular closure device 10.

Figure 3G:
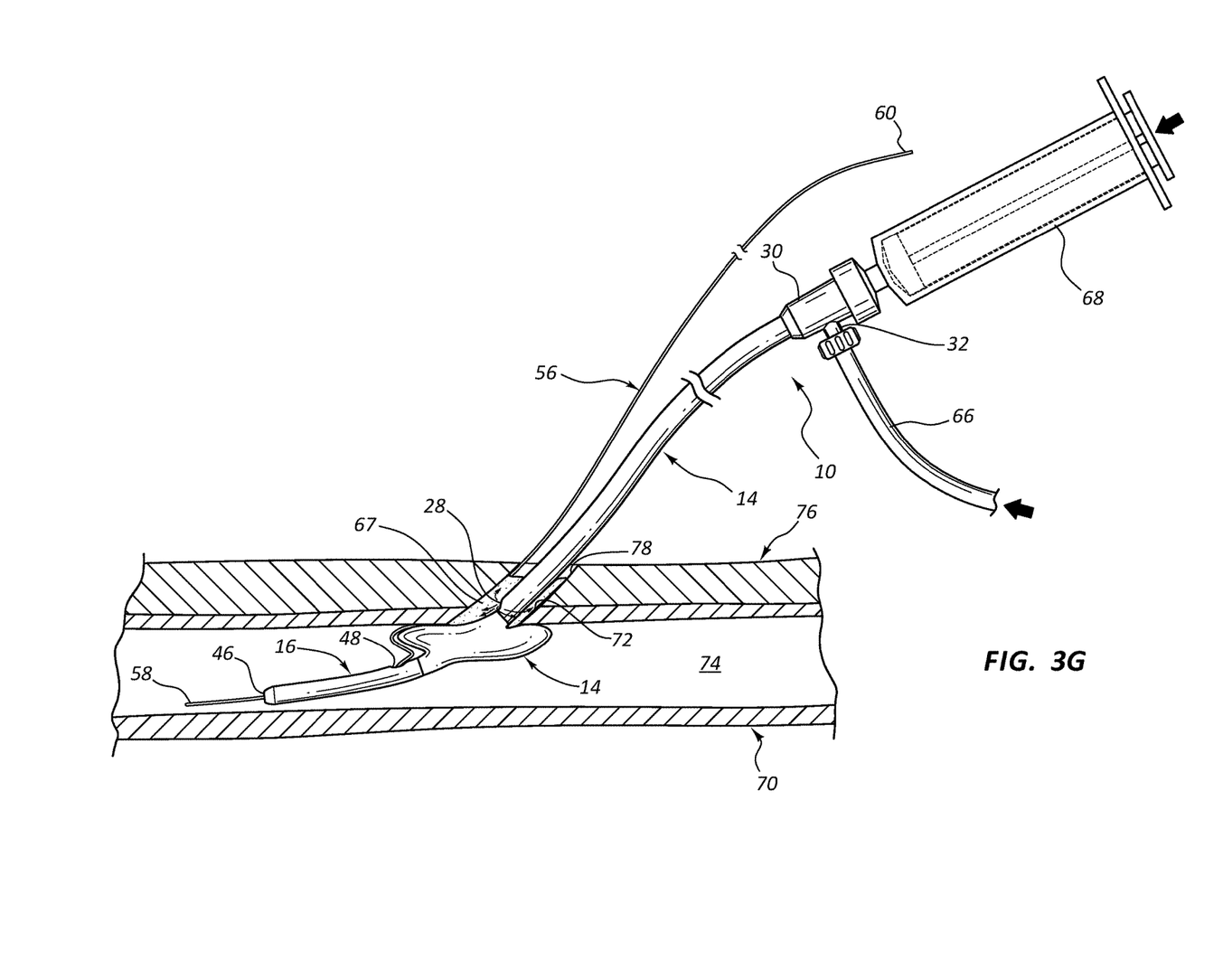

A sealant source 68 may be connected to the vascular closure device 10 to deliver a volume of sealing material 67 to the vessel puncture 72 as shown in FIG. 3G. The sealant source 68 may be in the form of, for example, a syringe, which when operated forces a volume of sealing material out through, for example, the distal port 28 of the blood flashback lumen 26. In other examples, a separate sealing material delivery device may be advanced through the tissue puncture 78 to deliver the volume of sealant to the vessel puncture 72 independent of the vascular closure device 10.

The sealing material 67 may be in the form of a flowable bio-compatible adhesive, also referred to as a bioadhesive. In other examples, the sealing material may be in the form of a preformed sealing plug comprising an expandable material such as, for example, collagen. The sealing material 67 may fill at least portions of the vessel puncture 72 and tissue puncture 78. Portions of the sealing material 67 may seal against an outer surface of the vessel 70 adjacent to the vessel puncture 72.

Figure 3H:
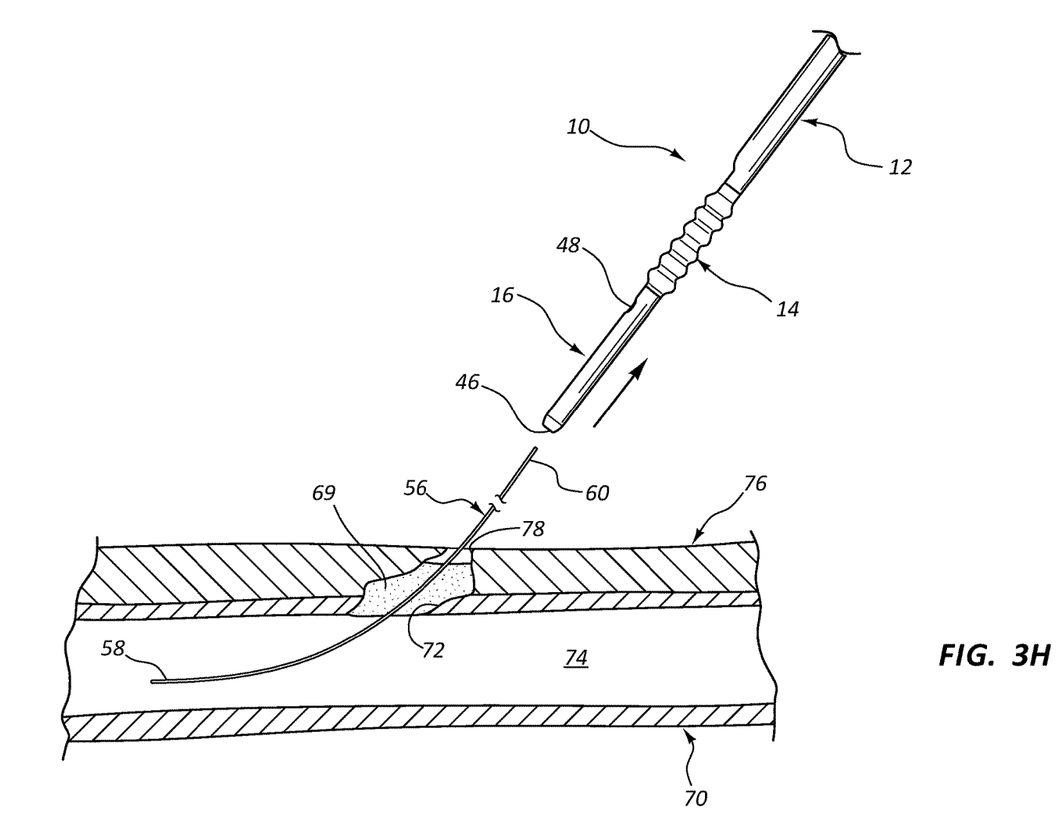

The sealing material 67 may cure to form a sealing plug 69 as shown in FIG. 3H. The sealing plug 69 may seal the vessel puncture 72 and at least a portion of the tissue puncture 78. The balloon 14 may be deflated and the vascular closure device 10 may be withdrawn along the guidewire 56 through the sealant plug 69 and out of the patient as shown in FIG. 3H. If the sealant plug 69 maintains closure of the vessel puncture 72 for a predetermined time, the operator may then remove the guidewire 56 through the sealant plug 69. The sealant plug 69 may close behind the guidewire 56 to provide complete hemostasis. Alternatively, an additional volume of sealing material may be delivered into the tissue puncture 78 proximal of the sealant plug 69 to further seal the vessel puncture and a tract remaining in the sealant plug 69 upon removal of the guidewire 56 and vascular closure device 10. Alternatively, the guidewire 56 may be removed concurrently with the vascular closure device 10 through the sealant plug 69.

Figure 4A:
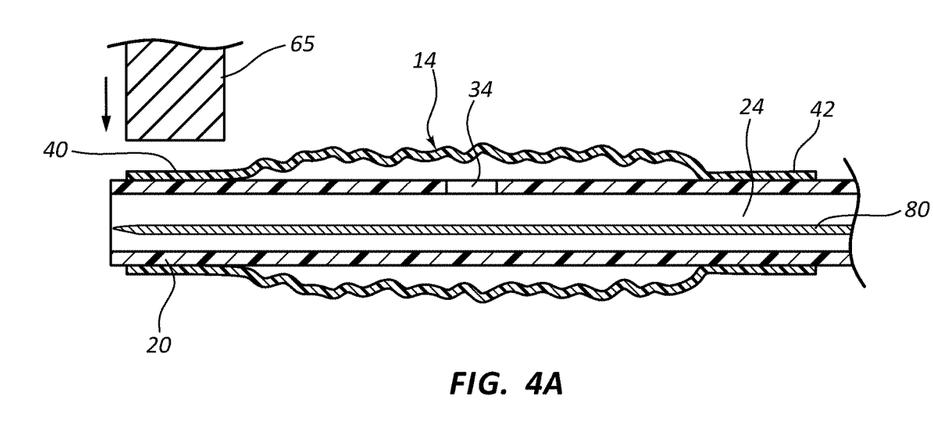
FIGS. 4A-4D show steps of forming a distal bond and rapid exchange port in the vascular closure device of FIG. 1.
Figure 4B:
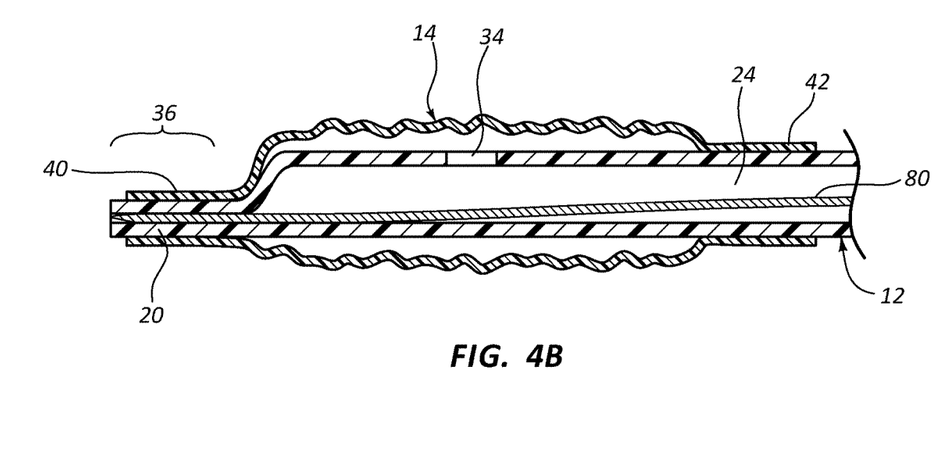

Referring now to FIGS. 4A-4D, an example method of forming the vascular closure device 10 is shown and described. FIG. 4A shows a distal end portion of the catheter shaft 12, the balloon 14, and a compression member 65. The balloon 14 includes distal and proximal waists 40, 42. The core wire 80 may be positioned within the inflation lumen 24 of the catheter shaft 12. The compression member 65 may be used to flatten or compress a distal end portion 20 of catheter shaft 12. The compression member 65 may concurrently compress or flatten the distal waist 40 of the balloon 14. FIG. 4B shows the catheter shaft 12 and balloon 14 having a flattened portion 36 at a distal end thereof and at least partially overlapping the distal waist 40 and distal end portion 20. The flattened portion 36 may overlap at least a portion of the core wire 80.

Figure 4C:
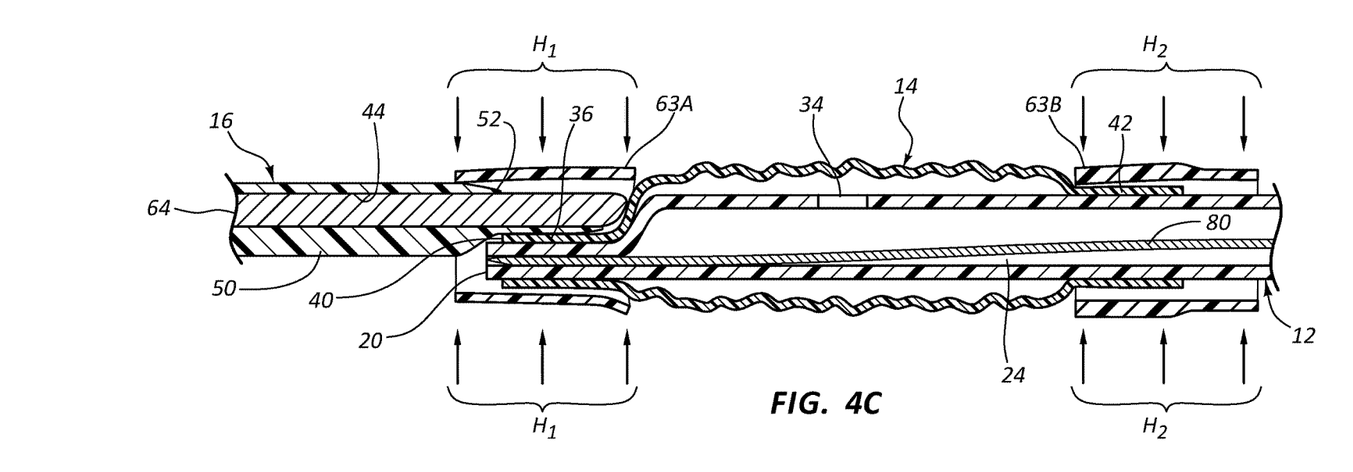

FIG. 4C shows the introducer 16 having a guidewire lumen 44 and a proximal end portion 50. A mandrel 64 extends through the guidewire lumen 44 and out through the proximal end portion 50. The proximal end portion 50 may have a slanted or tapered construction 52 (also referred to as a skive cut 52). A portion of the introducer 16 overlaps the flattened portion 36. At least a portion of the mandrel 64 may extend outside of the introducer 16 at the proximal end portion 50, and may at least partially overlap the flattened portion 36. Providing the skive cut 52 may expose additional length of the mandrel 64 while still providing at least some overlapping of the introducer 16 with the flattened portion 36.

Figure 4D:
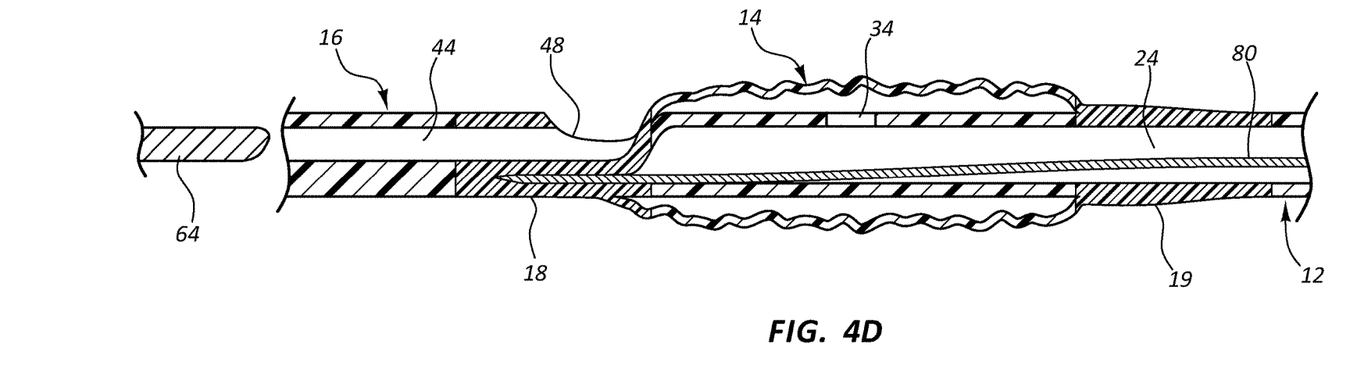

A heat sleeve 63A may be inserted over and overlap the skive cut 52, exposed portion of mandrel 64 and the flattened portion 36. A separate heat sleeve 63B may overlap the proximal waist 42 and a portion of the catheter shaft 12 arranged at a proximal end of balloon 14. Heat $H_1$ may be applied to the assembly at the distal end of the balloon 14, and separate heat $H_2$ may be applied at a proximal end of the balloon as shown in FIG. 4C. The applied heat $H_1$ may cause bonding of the introducer 16, distal waist 40 and catheter shaft 12 to form a distal bond 18 as shown in FIG. 4D. The heat sleeve 63A may be removed. The mandrel 64 may be removed to expose the proximal port 48 as a proximal guidewire port for the vascular closure device 10 at a location distal of the balloon 14. Heating with heat $H_1$ may create a flow of materials (e.g., various polymer materials) which were previously independent parts of the catheter shaft 12, balloon 14, and introducer 16. The heated materials may form an integral, homogeneous bond. The core wire 80 may be integrated into the distal bond 18. A separate proximal bond 19 may be formed between the proximal waist 42 and the catheter shaft 12 as shown in FIG. 4D.

The distal bond 18 may define not only a connection point or bond between the catheter shaft 12, balloon 14, and introducer 16, but may also define the proximal port 48 of the guidewire lumen 44. Other constructions are possible for the vascular closure device 10 in which, for example, the proximal port of the guidewire lumen 44 is formed and positioned at a location separate from the distal bond 18. In still further examples, the distal bond 18 may be formed solely between the introducer 16 and the balloon 14, or between only the introducer 16 and the catheter shaft 12. The proximal port 48 may be formed concurrently and integrally with these alternative bond constructions.

Figure 5A:
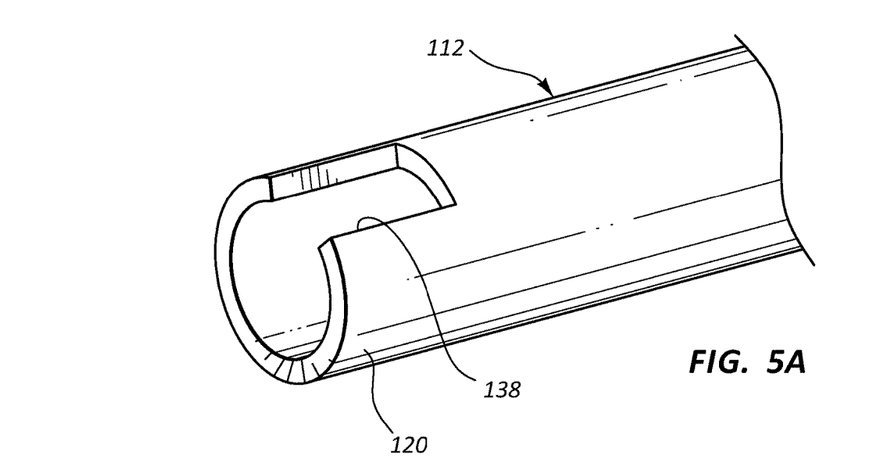
FIGS. 5A-5C show a distal end portion of a catheter shaft of the vascular closure device of FIG. 1 prior to forming the distal bond.
Figure 5B:
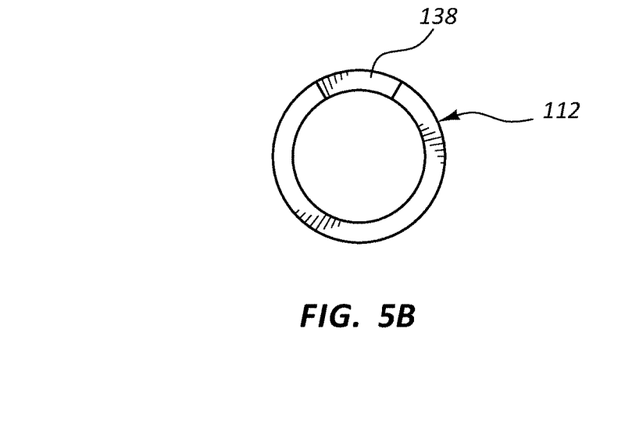
Figure 5C:
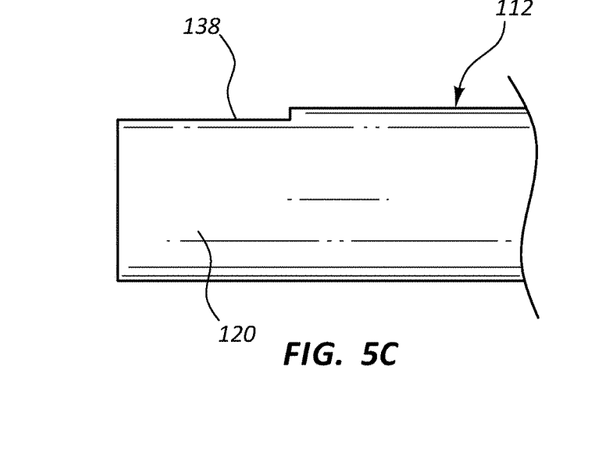

Referring now to FIGS. 5A-5C, an alternative catheter shaft 112 is shown having a cut out 138 at the distal end 120. The cut out 138 may be aligned with the distal waist of the balloon and may overlap with a proximal end portion of the introducer as part of creating the distal bond. By removing a portion of the catheter shaft 112 to form the cut out 138, an outer profile of the vascular closure device may be further reduced in the area of the distal bond. The cut out 138 may be used in conjunction with creating a flattened portion as described above with reference to FIGS. 4A-4D before forming the distal bond.

The guidewires disclosed herein may include, for example, a 0.014 inch to about a 0.018 inch diameter wire. In other examples, the guidewire may have a size in the range of about 0.02 inches to about 0.03 inches, and more particularly in the range of about 0.25 inches to about 0.026 inches. The guidewire may include a J-shaped distal tip. The mandrel disclosed herein may comprise a Teflon coating to assist in removing the mandrel after forming the distal bond.

Providing a guidewire rapid exchange port distal of the anchor (e.g., balloon) of a balloon catheter may have other applications in addition to the vascular closure devices disclosed herein. Providing a rapid exchange port distal of the temporary sealing anchor for an intravascular device may permit sheathless delivery of the device for at least those reasons discussed above.

The preceding description has been presented only to illustrate and describe exemplary embodiments of the present disclosure. It is not intended to be exhaustive or to limit the invention to any precise form disclosed. Many modifications and variations are possible in light of the above teaching. It is intended that the scope of the invention be defined by the following claims.

What is claimed is:

1. A vascular closure device, comprising:
    a catheter having an inflation lumen;
    a balloon positioned at a distal end portion of the catheter, the catheter and inflation lumen extending through the balloon;
    an introducer positioned distal of the balloon;
    a guidewire lumen extending along at least a portion of the introducer and terminating at a rapid exchange port positioned distal of the balloon, the guidewire lumen receptive of a guidewire to guide the catheter through a vessel puncture in a vessel to position the balloon within the vessel;
    wherein the inflation lumen, balloon and introducer are heat bonded together to form an integral, homogenous distal bond;
    wherein the distal bond is positioned between the catheter and the introducer and comprises a side surface,
    wherein the rapid exchange port opens radially from the side surface of the distal bond;
    a stiffening wire extending along at least a portion of the catheter to the rapid exchange port, the stiffening wire being bonded to the distal bond;
    a sealing material deliverable to the vessel puncture through the catheter and configured to seal the vessel puncture extravascularly.

2. The vascular closure device of claim 1, wherein the rapid exchange port is positioned at the distal bond between the catheter and the introducer.

3. The vascular closure device of claim 1, wherein the rapid exchange port is positioned at a distal bond location between the introducer and a distal waist of the balloon.

4. The vascular closure device of claim 1, wherein the stiffening wire is positioned in the inflation lumen.

5. The vascular closure device of claim 1, wherein the guidewire lumen extends from a distal tip of the introducer proximally to the rapid exchange port.

6. The vascular closure device of claim 1, wherein the balloon, when inflated, is configured to abut against an internal wall of the vessel to temporarily seal the vessel puncture.

7. The vascular closure device of claim 1, wherein the catheter includes a blood flashback lumen having a distal opening at a location proximal of the balloon.

8. A vascular closure device, comprising:
    an inflation tube having an inflation lumen, the inflation lumen comprising at least one radially-opening inflation outlet;
    a balloon mounted to the inflation tube and arranged in flow communication with the inflation lumen, the balloon being inflatable to temporarily seal a vessel puncture intravascularly, the inflation tube and inflation lumen extending through the balloon, the at least one radially-opening inflation outlet being positioned within the balloon;
    an introducer positioned distal of the balloon;
    a guidewire lumen extending distally from the balloon from a proximal port to a distal port, the guidewire lumen being receptive of a guidewire;
    wherein the inflation tube, balloon and introducer are heat bonded together to form an integral, homogenous distal bond;
    wherein the distal bond is positioned between the catheter and the introducer;
    a core wire positioned in the inflation lumen, the core wire being bonded to the distal bond, the proximal port of the guidewire lumen being positioned in a side surface of the distal bond and opening radially relative to the inflation lumen;
    wherein the vascular closure device is configured for advancement along the guidewire and through the vessel puncture;
    a sealing material deliverable to the vessel puncture through the catheter and configured to seal the vessel puncture extravascularly.

9. The vascular closure device of claim 8, wherein the inflation tube further includes a blood flashback lumen having a distal opening arranged proximal of the balloon.

10. The vascular closure device of claim 8, wherein the core wire extends proximally from the proximal port of the guidewire lumen.

11. The vascular closure device of claim 8, wherein the distal bond is arranged between a distal waist of the balloon and the inflation tube, the proximal port of the guidewire lumen being positioned at the distal bond.

* * * * *